(12) United States Patent
Norrby et al.

(10) Patent No.: US 8,298,205 B2
(45) Date of Patent: Oct. 30, 2012

(54) ELASTIC LAMINATE AND ABSORBENT ARTICLE COMPRISING THE LAMINATE

(75) Inventors: Niclas Norrby, Göteborg (SE); Jan Wästlund-Karlsson, Mölndal (SE)

(73) Assignee: SCA Hygiene Products AB, Göteborg (SE)

( * ) Notice: Subject to any disclaimer, the term of this patent is extended or adjusted under 35 U.S.C. 154(b) by 376 days.

(21) Appl. No.: 12/447,694

(22) PCT Filed: Nov. 13, 2006

(86) PCT No.: PCT/SE2006/050470
§ 371 (c)(1),
(2), (4) Date: Apr. 29, 2009

(87) PCT Pub. No.: WO2008/060204
PCT Pub. Date: May 22, 2008

(65) Prior Publication Data
US 2010/0076390 A1    Mar. 25, 2010

(51) Int. Cl.
*A61F 13/15* (2006.01)

(52) U.S. Cl. ......... 604/385.24; 604/385.25; 604/385.26; 604/385.36; 604/385.31; 604/396

(58) Field of Classification Search ............. 604/385.24, 604/385.25, 385.26, 385.3, 385.31, 396
See application file for complete search history.

(56) References Cited

U.S. PATENT DOCUMENTS

| | | | |
|---|---|---|---|
| 3,424,162 A | 1/1969 | Parravicini | |
| 4,119,450 A | 10/1978 | Bianco | |
| 4,663,220 A * | 5/1987 | Wisneski et al. | 428/221 |
| 4,698,261 A | 10/1987 | Bothe et al. | |
| 4,739,012 A | 4/1988 | Hagman | |
| 4,777,080 A | 10/1988 | Harris, Jr. et al. | |
| 4,842,596 A | 6/1989 | Kielpikowski et al. | |
| 4,932,949 A | 6/1990 | Thygesen et al. | |
| 5,114,781 A * | 5/1992 | Morman | 428/198 |
| 5,143,679 A | 9/1992 | Weber et al. | |
| 5,156,793 A | 10/1992 | Buell et al. | |
| 5,167,897 A | 12/1992 | Weber et al. | |

(Continued)

FOREIGN PATENT DOCUMENTS

CO    2007-0003796    12/2005

(Continued)

OTHER PUBLICATIONS

Hildeberg et. al, Copending U.S. Appl. No. 11/630,371, filed Dec. 21, 2006 entitled "Absorbent Article Comprising an Elastic Laminate Material".

Karlson et al., Copending U.S. Appl. No. 11/576,497, filed Dec. 3, 2008 entitled "Absorbent Article Comprising an Elastic Web Material".

(Continued)

*Primary Examiner* — Jacqueline F. Stephens
(74) *Attorney, Agent, or Firm* — Buchanan Ingersoll & Rooney PC

(57) ABSTRACT

An elastically stretchable laminate (1) includes a first non-elastic nonwoven web (2), a second non-elastic nonwoven web (4) and an elastic film (6) between the first and the second nonwoven webs (2,4). The laminate (1) has been rendered elastic in a first direction (MD) by incremental stretching and partial tearing of the first and second nonwoven webs (2,4). The laminate (1) includes a reinforcement layer (8) arranged between the first and second non-elastic nonwoven webs (2,4) and comprising unbroken reinforcement fibers or filaments (9) extending in a second direction (CD), generally perpendicular to the first direction (MD). Also described is a pant-type article including the elastically stretchable laminate.

30 Claims, 5 Drawing Sheets

U.S. PATENT DOCUMENTS

| | | | |
|---|---|---|---|
| 5,261,899 | A | 11/1993 | Visscher et al. |
| 5,336,545 | A | 8/1994 | Morman |
| 5,422,172 | A | 6/1995 | Wu |
| 5,440,764 | A | 8/1995 | Matsushita |
| 5,462,541 | A | 10/1995 | Bruemmer et al. |
| 5,514,470 | A * | 5/1996 | Haffner et al. ............... 428/343 |
| 5,592,690 | A | 1/1997 | Wu |
| 5,628,738 | A | 5/1997 | Suekane |
| 5,634,216 | A | 6/1997 | Wu |
| 5,635,290 | A | 6/1997 | Stopper et al. |
| 5,706,524 | A | 1/1998 | Herrin et al. |
| 5,733,628 | A | 3/1998 | Pelkie |
| 5,746,730 | A | 5/1998 | Suzuki et al. |
| 5,769,838 | A | 6/1998 | Buell et al. |
| 5,861,074 | A | 1/1999 | Wu |
| 5,921,973 | A | 7/1999 | Newkirk et al. |
| 6,072,005 | A | 6/2000 | Kobylivker et al. |
| 6,106,925 | A | 8/2000 | Palumbo |
| 6,210,386 | B1 | 4/2001 | Inoue |
| 6,240,569 | B1 | 6/2001 | van Gompel et al. |
| 6,476,289 | B1 | 11/2002 | Buell et al. |
| 6,540,731 | B2 | 4/2003 | Magnusson et al. |
| 6,552,245 | B1 | 4/2003 | Roessler et al. |
| 6,585,713 | B1 * | 7/2003 | LeMahieu et al. ............ 604/392 |
| 6,627,564 | B1 | 9/2003 | Morman et al. |
| 6,914,018 | B1 | 7/2005 | Uitenbroek et al. |
| 7,722,591 | B2 | 5/2010 | Back |
| 2002/0002021 | A1 | 1/2002 | May et al. |
| 2002/0019187 | A1 | 2/2002 | Carroll et al. |
| 2002/0029026 | A1 | 3/2002 | Furuya et al. |
| 2002/0052591 | A1 | 5/2002 | Zehner et al. |
| 2003/0022582 | A1 | 1/2003 | Cree et al. |
| 2003/0078558 | A1 | 4/2003 | Karami et al. |
| 2004/0078018 | A1 | 4/2004 | Van Gompel et al. |
| 2004/0102746 | A1 | 5/2004 | Mortell et al. |
| 2004/0116887 | A1 | 6/2004 | Thorson et al. |
| 2004/0122405 | A1 | 6/2004 | Van Gompel et al. |
| 2004/0122406 | A1 | 6/2004 | Moser et al. |
| 2004/0127878 | A1 | 7/2004 | Olson et al. |
| 2004/0133180 | A1 | 7/2004 | Mori et al. |
| 2004/0192140 | A1 | 9/2004 | Schneider et al. |
| 2004/0197588 | A1 | 10/2004 | Thomas et al. |
| 2004/0241389 | A1 | 12/2004 | Chung et al. |
| 2004/0243086 | A1 | 12/2004 | Van Gompel et al. |
| 2005/0010186 | A1 | 1/2005 | Otsubo et al. |
| 2005/0101216 | A1 | 5/2005 | Middlesworth et al. |
| 2005/0106980 | A1 | 5/2005 | Abed et al. |
| 2006/0148358 | A1 | 7/2006 | Hall et al. |
| 2007/0233034 | A1 | 10/2007 | Hildeberg et al. |
| 2008/0000003 | A1 | 1/2008 | Melander |
| 2008/0033387 | A1 | 2/2008 | Wastlund-Karlson et al. |
| 2009/0306616 | A1 | 12/2009 | Wennerback |

FOREIGN PATENT DOCUMENTS

| | | |
|---|---|---|
| CO | 2007-0003796 | 1/2008 |
| EP | 0 287 388 A2 | 10/1988 |
| EP | 0 304 957 A2 | 3/1989 |
| EP | 0 360 929 A1 | 4/1990 |
| EP | 0 409 307 B1 | 1/1991 |
| EP | 0 418 493 A1 | 3/1991 |
| EP | 0 486 006 B1 | 9/1996 |
| EP | 0 861 647 A2 | 9/1998 |
| EP | 0 714 351 | 12/1998 |
| EP | 0 605 012 B1 | 3/1999 |
| EP | 0 604 731 B1 | 6/1999 |
| EP | 1 184 022 | 3/2002 |
| EP | 1 035 818 B1 | 4/2002 |
| EP | 1 384 459 A2 | 7/2003 |
| EP | 1 473 008 | 11/2004 |
| FR | 2 586 558 | 3/1987 |
| FR | 2 810 879 | 1/2002 |
| GB | 2 284 538 A | 6/1995 |
| JP | 06255006 A | 9/1994 |
| JP | 07-252762 | 10/1995 |
| JP | 9-286085 | 11/1997 |
| JP | 10-043235 A | 2/1998 |
| JP | 2002 058 703 A | 2/2002 |
| JP | 2002-065740 | 3/2002 |
| JP | 2002-172137 A | 6/2002 |
| JP | 2002-520090 T | 7/2002 |
| JP | 2002-273808 A | 9/2002 |
| JP | 2003-520146 | 7/2003 |
| JP | 2003-290284 | 10/2003 |
| JP | 2004-050621 A | 2/2004 |
| JP | 2004-098356 A | 4/2004 |
| JP | 2004-519270 | 7/2004 |
| RU | 2 008 774 | 3/1994 |
| RU | 2 221 531 | 1/2004 |
| SU | 965339 | 10/1982 |
| SU | 965339 A | 10/1982 |
| TW | 233473 | 11/1994 |
| WO | WO 95/19258 | 7/1995 |
| WO | WO 96/10979 A1 | 4/1996 |
| WO | WO 97/29722 A1 | 8/1997 |
| WO | WO 97/34037 A1 | 9/1997 |
| WO | WO 98/37847 A1 | 9/1998 |
| WO | WO 99/27876 A1 | 6/1999 |
| WO | WO 99/32164 A1 | 7/1999 |
| WO | WO 00/02511 A1 | 1/2000 |
| WO | WO 00/45764 A1 | 8/2000 |
| WO | WO 01/30563 A1 | 5/2001 |
| WO | WO 01/45927 A1 | 6/2001 |
| WO | WO 01/53076 | 7/2001 |
| WO | WO 02/34185 | 5/2002 |
| WO | WO 02/49560 A1 | 6/2002 |
| WO | WO 03/004748 A1 | 1/2003 |
| WO | WO 03/019714 A1 | 3/2003 |
| WO | WO 03/047488 A1 | 6/2003 |
| WO | WO 2004/058120 | 7/2004 |
| WO | WO 2004/060251 A1 | 7/2004 |
| WO | WO 2004/078083 A1 | 9/2004 |
| WO | WO 2005/095700 A1 | 10/2005 |
| WO | WO 2005/122984 A1 | 12/2005 |
| WO | WO 2005/122985 A1 | 12/2005 |
| WO | WO 2005122985 * | 12/2005 |
| WO | WO 2006/038837 A1 | 4/2006 |
| WO | WO 2006/093439 A1 | 9/2006 |
| WO | WO 2006/093440 A1 | 9/2006 |
| WO | WO 2006/093443 A1 | 9/2006 |
| WO | WO 2007/114744 A1 | 10/2007 |
| WO | WO 2008/060194 A1 | 5/2008 |

OTHER PUBLICATIONS

Wastlund-Karlssson et al., Copending U.S. Appl. No. 11/630,372, filed Dec. 21, 2006 entitled "Absorbent Article Comprising an Elastic Laminate".

Melander, Copending U.S. Appl. No. 11/845,153, filed Aug. 27, 2007 entitled "Underwear Article Comprising an Elastic Laminate".

Wennerback, Copending U.S. Appl. No. 12/446,297, filed Apr. 20, 2009 entitled "Absorbent Article Comprising an Elastic Laminate".

Wennerback, Copending U.S. Appl. No. 12/514,086, filed May 8, 2009 entitled "Absorbent Article Comprising an Elastic Laminate Material".

Non-Final Office Action in Copending U.S. Appl. No. 11/630,372 to Wastlund-Karlson et al. dated Sep. 16, 2009.

Final Office Action in Copending U.S. Appl. No. 11/630,372 to Wastlund-Karlson et al. dated Mar. 2, 2008.

Non-Final Office Action in Copending U.S. Appl. No. 11/630,372 to Wastlund-Karlson et al. dated Jul. 8, 2009.

Non-Final Office Action in Copending U.S. Appl. No. 11/630,371 to Hildeberg et al. dated Oct. 5, 2009.

Sueo Kawabata, "The Standardization and Analysis of Hand Evaluation", Second Edition, The Hand Evaluation and Standardization Committee, The Textile Machinery Society of Japan, published by the Textile Machinery Society of Japan, Osaka, Japan, Jul. 1980—Textile Machinery Japan.

PCT/ISA/210 completed Jun. 21, 2007.

PCT/ISA/237 completed Jun. 21, 2007.

An English Translation of the Notice of Reasons for Rejection issued in the corresponding Japanese Patent Application No. 2007-517994 dated Nov. 24, 2009.

* cited by examiner

ELASTIC LAMINATE AND ABSORBENT ARTICLE COMPRISING THE LAMINATE

TECHNICAL FIELD

The invention pertains to an elastically stretchable laminate comprising a first non-elastic nonwoven web, a second non-elastic nonwoven web and an elastic film between the first and the second nonwoven webs, wherein the laminate has been rendered elastic in a first direction by incremental stretching and partial tearing of the first nonwoven webs.

BACKGROUND ART

Pant-type absorbent articles include a pant-shaped chassis structure and an absorbent core component integrated with the chassis. A major objective when designing pant articles is to make them resemble ordinary underwear as closely as possible. Hence, absorbent articles such as pant diapers, sanitary pants and incontinence pants are designed to fit comfortably and snugly about the wearer. It is desirable that the articles are capable of being pulled up and down over the hips of the wearer to allow the wearer or caregiver to easily remove a soiled article and to replace it with a new clean one. For these reasons, the article chassis is usually made of a material that is elastically stretchable, at least in the areas intended to be applied over the wearer's hips. Furthermore, it is desirable that the chassis surrounding the absorbent parts of the pant-type article is permeable to air and vapour, i.e. that it is breathable. A breathable article prevents moisture from remaining on the skin of the wearer and is more comfortable and less warm to wear than a non-breathable article. It is also beneficial if the article is soft, smooth and textile-like, so that it does not chafe the skin of the wearer and so that it resembles ordinary underwear as closely as possible.

Moreover, it is important that the absorbent pant article can be pulled up over the hips of a wearer without rupturing. A common problem is that the wearer or the caregiver tears the pant by inadvertently poking the fingers through the material when trying to get a good grip for pulling up or removing the pant.

A previously used elastic material for pant articles is a laminate comprising an elastic film sandwiched between two layers of non-elastic nonwoven. In order to render the laminate elastically stretchable, it is subjected to an activation treatment. A three-layer, activated laminate is disclosed in International Patent Application No. WO 03/047488. The activated laminate is produced by incrementally stretching an elastic film layer between two non-elastic cloth-like layers. Incremental stretching is carried out by passing the laminate between intermeshing gear rollers. Activation of elastic laminates by incremental stretching is also disclosed in U.S. Pat. Nos. 5,143,679, 5,156,793 5,167,897, 5,422,172, 5,592,690, 5,634,216 and 5,861,074. The non-elastic cloth-like layers are fully or partially broken or torn during the activation process so that the elasticity of the laminate after activation is mainly governed by the elasticity of the elastic film layer. In the three-layer laminate in WO 03/047488, the non-elastic layers are completely broken so that the elasticity of the activated laminate is substantially the same as the elasticity of the elastic film layer.

The disclosed laminates have excellent comfort properties and are soft, breathable and elastic. However, a major disadvantage with the known laminates is that the activation process at least partially breaks and destroys the cloth-like layers resulting in a material having decreased tensile strength and puncture resistance. When used as a chassis component in a disposable pant article, the material is easily torn when exposed to the forces arising when putting on or pulling off the pant article. This tearing problem is particularly pronounced for female wearers or caregivers who often have long fingernails that may penetrate and tear the pant material.

Hence, there exists a need for an improved elastic laminate for use in pant-type absorbent articles having a chassis including one or more elastically stretchable textile-like panels. There is also a need for a pant-type absorbent article having a chassis with elastic portions with improved tensile strength and puncture resistance.

Accordingly, an object of the invention is to provide an elastically stretchable laminate for use in disposable pant-type absorbent articles having improved tensile strength and puncture resistance and to provide disposable pant-type absorbent articles having improved tensile strength and puncture resistance.

DISCLOSURE OF INVENTION

In accordance with the invention, there is provided an elastically stretchable laminate comprising a first non-elastic nonwoven web, a second non-elastic nonwoven web and an elastic film between the first and the second nonwoven webs wherein the laminate has been rendered elastic in a first direction by incremental stretching and partial tearing of the first and second nonwoven webs. The laminate further comprises a reinforcement layer arranged between the first and second non-elastic nonwoven webs and comprising unbroken reinforcement fibres or filaments extending in a second direction, generally perpendicular to the first direction.

Suitable reinforcement fibres and filaments are any natural or man-made fibres or filaments having sufficient length and tensile strength. Accordingly, cotton, regenerated cellulose, polymers such as polyolefins, polyesters, polyamides, etc. may be used in the form of mono or multi-component fibres or filaments.

Fibres are natural or man-made elongated structures having a defined length, and include cotton fibres, flax, hemp and staple fibres and fibrillated plastic films. By filaments are meant all types of filamental structures having an "endless" or "continuous" character such as meltspun polymer filaments, bands or elongated endless film fragments and natural or staple fibres that have been spun into threads.

Suitable fibres and filaments for use in the reinforcement layer in accordance with the invention are those having a length of at least 10 millimetres and preferably at least 20 millimetres.

As used herein, an elastic material is a material having a permanent elongation after relaxation of less than 10% after the material has been subjected to an elongation of 30% in the elasticity test specified in the description.

A non-elastic material is a material that does not fall within the definition of an elastic material. Accordingly, a non-elastic material as used herein is a material that may be stretchable or non-stretchable. In the case of a stretchable material, the material has a permanent elongation after stretching and relaxation of more than 10% after having been subjected to an elongation of 30% as determined according to the elasticity test.

Factors that influence the elasticity of the elastic laminate are the flexibility and extensibility of the non-elastic nonwoven layers. The amount of bonding between the layers in the laminate also affects the flexibility and elasticity of the elastic laminate. Accordingly, a large bonded area will decrease the elasticity in the laminate while sparsely distributed bonding points will have a very small or negligible influence on the elasticity.

The elastic film in the laminate is preferably perforated in order to provide breathability. This can be achieved directly in conjunction with the lamination process if, for instance, a first non-elastic nonwoven web is bonded to the elastic film by means of extrusion coating. The perforating step can be carried out by passing the combined elastic layer and nonwoven web over a vacuum lamination drum while the elastic layer is in a molten or semi-molten state. Such a process is disclosed in U.S. Pat. No. 5,733,628 and results in the elastic film being formed into a three-dimensional apertured laminate layer.

Alternatively, the elastic film can be a prefabricated perforated film that is bonded to the non-elastic nonwoven webs by any suitable means such as adhesively, thermally or with ultrasonic welding.

The activation step involves incremental stretching of the elastic laminate so that the non-elastic nonwoven webs are broken or torn, at least partially. Activation can be carried out by means of heated or non-heated intermeshing gear rollers having circumferentially arranged teeth that intermesh and thereby stretch the laminate. The activation step allows the laminate to be subsequently stretched in the direction of activation without being appreciably restrained by the non-elastic nonwoven webs. The degree of breaking of the non-elastic nonwoven material determines the maximum possible elongation for the resulting laminate. If the nonwoven material is completely broken in the activation process, the laminate will have substantially the same maximum elongation as the elastic film layer.

An unbroken fibre or filament as used herein, is a fibre or filament that has been incorporated in the elastic laminate prior to activation of the laminate but is left substantially unaffected by the activation process. Hence, the unbroken reinforcement fibres or filaments in the elastic laminate have the same length and tensile strength as before being subjected to the activation step.

In accordance with one embodiment of the invention, the reinforcement layer is an oriented fibrous nonwoven layer having more than 50% of the fibres oriented in the second direction and preferably more then 70% of the fibres oriented in the second direction. The fibres may be any suitable synthetic or natural fibres as set out above. When using polyaramid fibres the fibre thickness preferably is at least 5 dtex, more preferably at least 10 dtex but preferably not more than 40 dtex. For other fibres such as polyester, polypropylene, polyethylene fibres, etc. the fibre thickness preferably is at least 10 dtex but not more than 150 dtex.

A high degree of orientation means that a high proportion of the fibres will escape the activation process without being broken or damaged since the fibres will be aligned with the direction in which the laminate is broken and will be perpendicular to the direction of activation. In this manner the fibres oriented in the second direction will provide reinforcement perpendicular to the direction of elasticity in the laminate. This implies that when the laminate is incorporated in an absorbent pant-type article, for instance forming elastic side panels in the article, the reinforcement layer will allow the article to be pulled up over a user's hips when putting on the article and to subsequently be removed without risk of tearing or puncturing the elastic pant material Suitable ways of creating a high degree of orientation in a nonwoven material is by extruding, meltspinning, carding or hydroentangling the fibres in the material. Hence, suitable nonwovens used as reinforcement layers in the laminate according to the invention are meltblown, spunbond, spunlaced and carded nonwoven webs.

According to another embodiment of the invention, the reinforcement layer is a layer of filaments. The filaments may either be provided as individual filaments or may be used in the form of filament bundles also known as tow. The filaments may be bonded to a support layer or may be in the form of unbonded filaments. When using polyaramid fibres the fibre thickness preferably is at least 5 dtex, more preferably at least 10 dtex but preferably not more than 40 dtex. For other fibres such as polyester, polypropylene, polyethylene fibres, etc. the fibre thickness preferably is at least 10 dtex but not more than 150 dtex.

In order to avoid risking that the reinforced laminate is inadvertently broken by running the fingers through the laminate when trying to pull up a pair of disposable panties incorporating the laminate, the distance between individual fibres or filaments should not exceed 30 millimetres, preferably should not exceed 20 millimetres and most preferably should not exceed 15 millimetres. It is not critical that the distance between the fibres or filaments is precisely adapted to a finger's width, since the non-elastic nature and the tensile strength in the reinforcement fibres together with the bonds in the laminate counteract stretching and deformation of the material in the second direction.

In accordance with a particularly preferred embodiment of the invention, the reinforcement layer is a net. It is advantageous to use a net as a reinforcement layer, since the net can be readily incorporated in a continuous production process in a controlled manner such that the reinforcement filaments or strands in the net run in a direction perpendicular to the machine direction of the process. The filaments in the net can be chosen to have different tensile strength in the machine direction (MD), corresponding to the first direction in the laminate and in the cross direction (CD), corresponding to the second direction in the laminate.

The filaments of the net reinforcement layer arranged in the MD may be broken during activation of the laminate while the reinforcement filaments arranged in the CD are left intact. Accordingly, the net offers production advantages and provides an optimal combination of reinforcement and minimal negative influence on the elastic properties of the laminate.

Another way of achieving a favourable combination of good processability when incorporating the reinforcement layer in the laminate and the desired elasticity and strength in the activated laminate is by using a plastic film for the reinforcement layer. The film appears in the activated laminate as a plurality of elongated, band-shaped film fragments that have been created by breaking of the film during activation of the laminate.

In order to ascertain that the reinforcement layer will break in a predetermined and controlled manner when subjected to the tearing forces arising during activation of the elastic laminate, the reinforcement layer may have been provided with tear indications arranged in the second direction and along which the reinforcement layer has been fully or partially broken during activation of the laminate. The tear indications may be in the form of perforations, embossments, thinned portions of the film, etc.

In the laminate in accordance with the invention, at least one of the non-elastic nonwoven webs may be a creped nonwoven. Creped nonwovens generally have greater extensibility and flexibility than non-creped nonwovens.

A creped nonwoven material as used herein is any nonwoven material wherein the fibres have been crinkled or bulked, thermally or mechanically, to foreshorten the fibres in the direction of creping whereby the material becomes stretchable and preferably resiliently stretchable in the direction of the creped fibres. The nonwoven webs used in the invention may be creped both in the manufacturing direction, MD and in the cross direction CD. The creped nonwoven webs are preferably stretchable, more preferably resiliently or elastically stretchable in at least the MD implying that the webs will recover at least some of their initial dimensions after being stretched. If it is desirable to have stretch properties both in MD and CD, this may be achieved either by choosing a nonwoven web that is inherently CD stretchable or by two-directional creping. Recovery from stretching is strongly dependent of the fibre orientation. Hence, a web that is stretchable in the MD and has a majority of the fibres oriented in that direction will have better recovery properties than a more randomised web.

By choosing a creped nonwoven for one or both of the non-elastic nonwoven layers, it is possible to achieve an elastic laminate that is more conformable and extensible than when using non-creped nonwovens. The creped nonwoven makes it easier for the elastic laminate to contract after elongation, thus increasing the elasticity when compared to a corresponding laminate having only non-creped nonwoven layers.

One or both of the non-elastic fibrous nonwoven webs in the elastic laminate may preferably comprise thermoplastic fibres. Examples of suitable polymers for use in the nonwoven webs are polyethylene, polyesters, polypropylene and other polyolefin homopolymers and copolymers. Particularly well suited nonwoven webs are those comprising thermoplastic fibres that are a mixture of polypropylene and polyethylene fibres. The preferred webs have a high content of thermoplastic fibres and contain at least 50% thermoplastic fibres and preferably at least 80% thermoplastic fibres. The non-elastic nonwoven webs will typically be incorporated in joins and seams in a disposable pant-type article. Hence, it is highly desirable that the nonwoven webs be weldable by heat or by ultrasonic welding processes. For this reason, one or both of the non-elastic nonwoven webs may comprise at least 80% polypropylene fibres.

The fibrous layers are preferably chosen so as to provide a soft and cloth-like feel and appearance to the laminate. Examples of suitable materials are, meltblown, spunbond, and creped nonwovens, as set out above. However, any soft, flexible and preferably extensible nonwoven materials and nonwoven laminates may be used, such as Spunbond-Meltblown-Spunbond-laminates (SMS), carded bonded webs and spunlaced materials.

The basis weight of the non-elastic nonwoven webs used in the laminate is suitably from 10-80 g/m$^2$ and preferably from 13-50 g/m$^2$. Examples of suitable polymers used in the fibrous material are polyethylene, polyesters, polypropylene and other polyolefin homopolymers and copolymers. Natural fibres, for example cotton, may also be used as long as they provide the desired properties. A mixture of polymers can contribute to a higher flexibility of the nonwoven layer, and through this, give the nonwoven material a higher elongation at maximum load. A mixture of polyethylene and polypropylene polymers has proven to provide good results in this respect. A mixture of fibres of different polymers is also possible.

The elastic layer is preferably an apertured elastic film. The elastic layer may have a basis weight of between 10 and 120 g/m$^2$, preferably between 15 and 60 g/m$^2$. The elastic layer may be of any suitable elastic polymer, natural or synthetic. Some examples of useful materials for the elastic layer are low crystallinity polyethylenes, metallocene-catalyzed low crystallinity polyethylenes, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable elastic film is an apertured three-layer elastomeric film with the composition polyethylene-styrene/ethylene/butadiene/styrene-polyethylene (PE-SEBS-PE).

The elastic laminate in accordance with the invention can, for instance, be manufactured and activated according to either of the methods disclosed in WO 03/047488 or EP 0 715 351 by laminating a first nonwoven web to one side of the elastic film layer and the reinforcement layer and a second nonwoven web to the other side of the elastic film. The first nonwoven web and the film may be extrusion bonded or may be bonded by adhesive, thermal bonding or ultrasonic bonding. Similarly, the additional layers in the laminate may be extrusion bonded or may be adhesively, thermally or ultrasonically bonded.

After lamination, the laminate has been incrementally stretched to activate the elasticity of the elastic film layer. Incremental stretching can be made to a point below the elongation at peak load of the non-elastic nonwoven web to retain some strength in the nonwoven web. Alternatively, the stretching may be carried out so that the nonwoven is completely torn, as disclosed in WO 03/047488.

The invention also offers a pant-type absorbent article comprising a chassis structure comprising a front panel having a front end edge and first and second side edges, a back panel having a back end edge and first and second side edges and a crotch panel arranged between the front and back panels and front and back waist panels arranged at the front and back panels respectively, and a core component being integrated with the chassis structure, the first and second side edges of the front panel being joined by edge joins to the corresponding first and second side edges of the back panel, at least one of the front and back panels comprising an elastic laminate comprising a first non-elastic nonwoven web, a second non-elastic nonwoven web and an elastic film between the first and the second nonwoven webs wherein the laminate has been rendered elastic in a first direction by incremental stretching and partial tearing of the first and second nonwoven webs. In accordance with the invention, the elastic laminate further comprises a reinforcement layer arranged between the first and second non-elastic nonwoven webs and comprising unbroken reinforcement fibres or filaments extending in a second direction, generally perpendicular to the first direction.

The reinforced elastic laminate in accordance with the invention may form one or both of the front and back panels of the pant-type absorbent article.

However, it is not necessary that all of the front and back panels are constituted by the elastic laminate according to the invention. Hence, the elastic laminate chassis portions may constitute at least 20%, preferably at least 25%, more preferably at least 30% and most preferably at least 40% of the total surface area of the chassis.

It is preferred that at least one of the waist panels of the pant-type article according to the invention comprises an elastic waist feature.

The waist panels can be joined to the front and back panels as separate components in a pant-forming process. The waist panels may comprise an elastic waist feature in the form of an elastic band of any suitable kind, such as elastic laminates, elastic foam strips, elastic nonwovens, non-elastic materials that have been elasticised with elastic threads or strings, etc.

A commonly used elastic waist feature is made by attaching elastic elements such as threads, bands or strings in a pre-tensioned state between two layers of nonwoven, non-elastic material. All commonly used elastic materials such as natural or synthetic rubber, elastic foam, etc. can be employed. A waist feature of this type may be formed from two separate layers of nonwoven or may be made from a single layer of nonwoven that has been folded into a two-layer structure. It is also possible to use the activated reinforced laminate in accordance with the invention to create an elastic waist feature. The elastic waist feature in the waist panels preferably has a higher elastic tension than the elastic panel portions in other parts of the chassis.

In an alternative embodiment, the elastic waist feature is an integral part of the chassis. In this embodiment, the elastic waist feature may have been formed by folding an edge portion of a non-elastic chassis web and attaching elastic elements between the folded portions of the chassis web. It is also possible to attach elastic elements to a layer of the chassis web and leave the elastic elements non-covered, or covered by a separate web. A further option is to create an elastic waist feature by folding an edge portion of an elastic front and/or back panel, thus creating a waist panel having higher elastic tension than the non-folded portions of the elastic panels. Elastic waist features suitable for use in the pant-type absorbent article in accordance with the invention are disclosed in PCT/SE205/000309.

BRIEF DESCRIPTION OF DRAWINGS

The invention will in the following be described in greater detail with reference to the appended drawings, wherein.

EMBODIMENTS OF THE INVENTION

Figure 1:
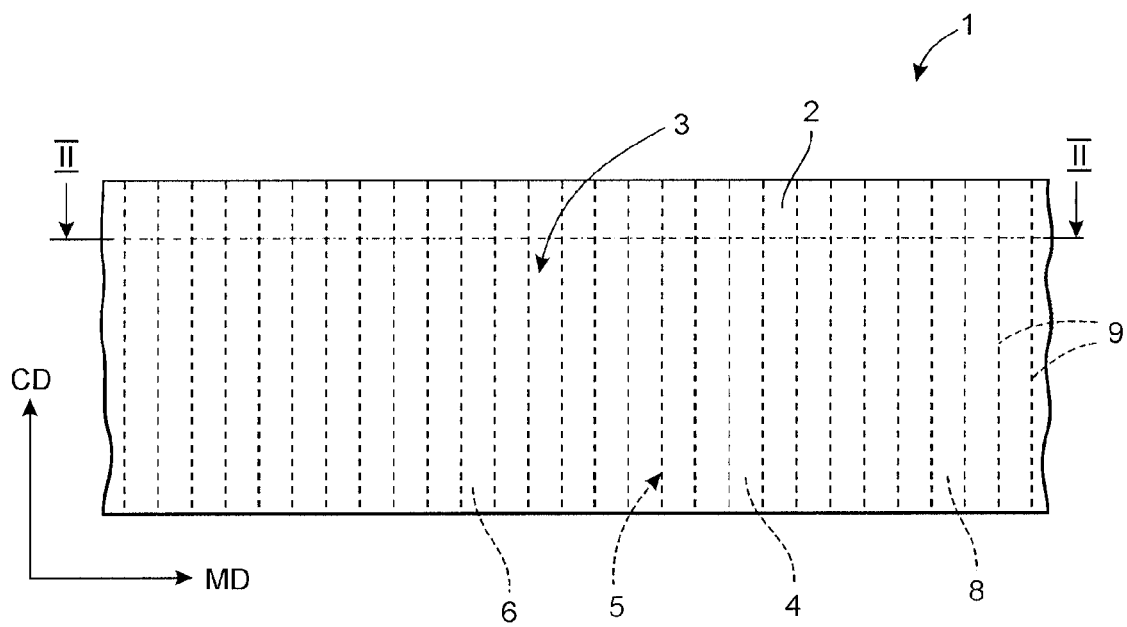
FIG. 1 shows schematically a reinforced laminate in accordance with the invention.
Figure 2:
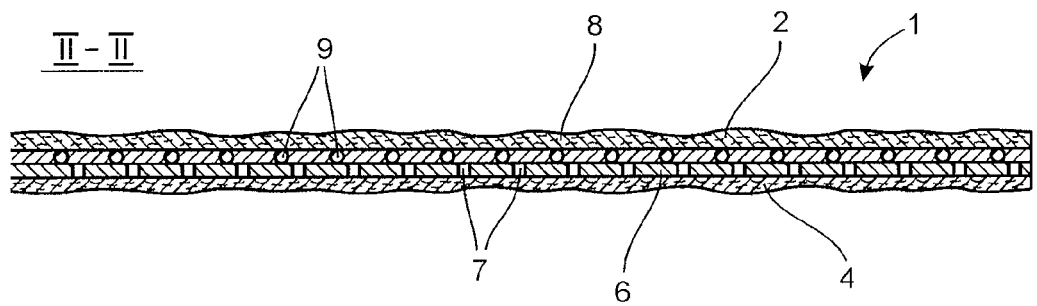
FIG. 2 shows a section taken along the line II-II through the laminate in FIG. 1.

The laminate 1 shown in FIGS. 1 and 2 comprises a first non-elastic outer nonwoven layer 2 forming a first surface 3 of the laminate and a second non-elastic outer nonwoven layer 4 forming a second surface 5 of the laminate 1.

An elastic film 6 is arranged between the outer nonwoven layers 2,4. The elastic film 6 is shown as an apertured film and has a multiplicity of apertures 7 arranged therethrough. The apertures 7 may be three-dimensionally formed apertures as disclosed in WO 03/047488 or may be simple two-dimensional holes through the film. The elastic film is elastically extensible at least in a first direction, MD. For a laminate produced in a continuous process, the first direction, MD is the machine direction, i.e. the travelling direction of the laminate web during production of the web. The laminate is elastically extensible in the first direction MD and may be extensible or elastically extensible also in a second direction, the cross direction CD, perpendicular to the first direction MD or may be non-elastic or non-stretchable in the CD.

The laminate 1 further includes a reinforcement layer 8 having a plurality of reinforcement fibres or filaments 9 extending in the second direction, CD. The reinforcement fibres or filaments 9 provide the laminate 1 with high tensile strength in the second direction, CD and also with high puncture resistance.

The laminate 1 has been subjected to an activation treatment by means of incremental stretching of the laminate 1 to partially or fully break up the outer nonwoven layers 2,4 and allow the laminate to be elastically stretchable in the first direction, MD. Hence, the activation process tears and breaks fibres and bonds in the outer nonwoven layers 2,4, primarily along tear lines oriented in the second direction CD, making the outer nonwoven layers 2,4 softer and more bulky than before the activation process, but also considerably weakened, with low tensile strength and poor puncture resistance.

Since the activation process involves tearing of the material substantially only along deformation lines running in the second direction CD, the activation process leaves the reinforcement fibres or filaments 9 in the reinforcement layer 8 substantially unaffected. Hence, substantially all of the reinforcement fibres or filaments 9 will remain unbroken also after the laminate has been subjected to activation. However, any non-elastic or non-stretchable fibres or other material in the reinforcement layer 8 extending in the first direction, MD, will be torn or broken in the activation process.

The non-elastic outer nonwoven layers 2,4 are preferably soft, conformable and optionally stretchable materials, as previously disclosed. Moreover, by selecting nonwoven materials having thermoplastic properties, it is possible to obtain a laminate that can be readily incorporated in a disposable article by thermo-welding techniques. Accordingly, it may be beneficial if one or both of the outer nonwoven layers are partially or completely made of thermoplastic fibres, such as polypropylene fibres. The outer nonwoven layers 2,4 can then be used to form side joins with good tensile strength in a pant-type article. Since thereto-bonds used in side joins usually penetrate the welded materials, the orientation of the laminate with respect to the first and second outer nonwoven layers 2,4 is normally not crucial for obtaining a thermo-bonded join as long as at least one of the layers is predominantly made of thermoplastic fibres or the combined layers in the laminate 1 contain sufficient thermoplastic material in order to achieve satisfactory bond strength.

Side joins are often arranged in a pant-type article to connect the article's front portion to the rear portion and to form a pant having a waist opening and leg openings. Usually, the side joins are intended to be arranged at the user's hips during use of the absorbent pants, but it is also known to arrange side joins more to the front of the article. The side joins are preferably designed so that they can withstand the tensile forces which arise when the article is being put on and is being worn, but such that they can be torn apart or opened in a controlled manner when the absorbent pants are taken off or to check if the article needs changing. In the latter instance, the side joins are preferably reclosable joins, as known in the art.

Lamination of the different layers in the laminate may be made in any suitable manner, such as by extrusion coating, by adhesive, by stitching or by ultrasonic welding or thermo-welding. Any commonly used type of adhesive may be used, such as curable adhesives, solvent based adhesives or thermoplastic adhesives.

Figure 3:
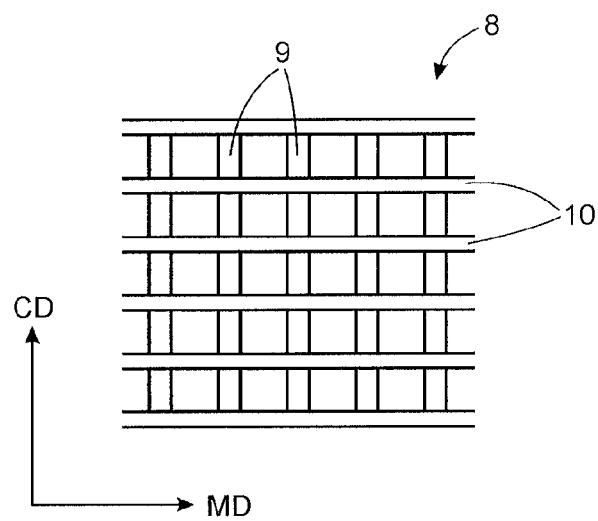
FIG. 3 shows a reinforcement layer in the form of a net.

In FIG. 3 is shown a reinforcement layer 8 in the form of a net. The net has a plurality of reinforcement filaments 9 arranged in the second direction CD and connecting strands 10 arranged in the first direction MD, perpendicular to the reinforcement filaments 9. The connecting strands 10 serve the primary purpose of keeping the reinforcement filaments 9 at a proper distance and disposition during manufacturing of the elastic laminate 1 in accordance with the invention. Hence, once the layers of the laminate are secured to each other, the connecting strands 10 may be broken in the activation step together with the outer non-elastic nonwoven webs. Alternatively, the connecting strands 10 may be elastic, at least to the same extent as the elastic film 6, or may be made of a hot melt adhesive material that can be melted and used to bond the adjacent layers in the laminate 1.

The reinforcement filaments 9 and the connecting strands 10 may be joined to each other by any suitable means such as adhesively, mechanically or by thermal bonding. The filaments 9 and strands may be arranged in the way shown in FIG. 3 with all reinforcement filaments 9 in a first plane and all connecting strands 10 in a second plane or may be intermeshed or interwoven in any suitable manner.

Figure 4:
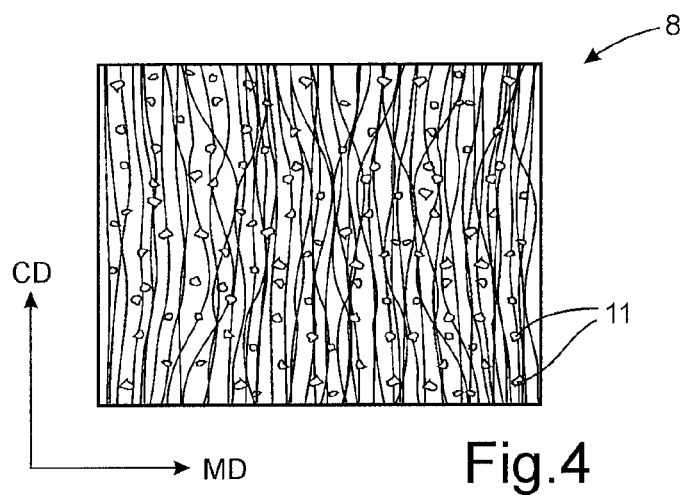
FIG. 4 shows a reinforcement layer in the form of an oriented nonwoven.
Figure 8:
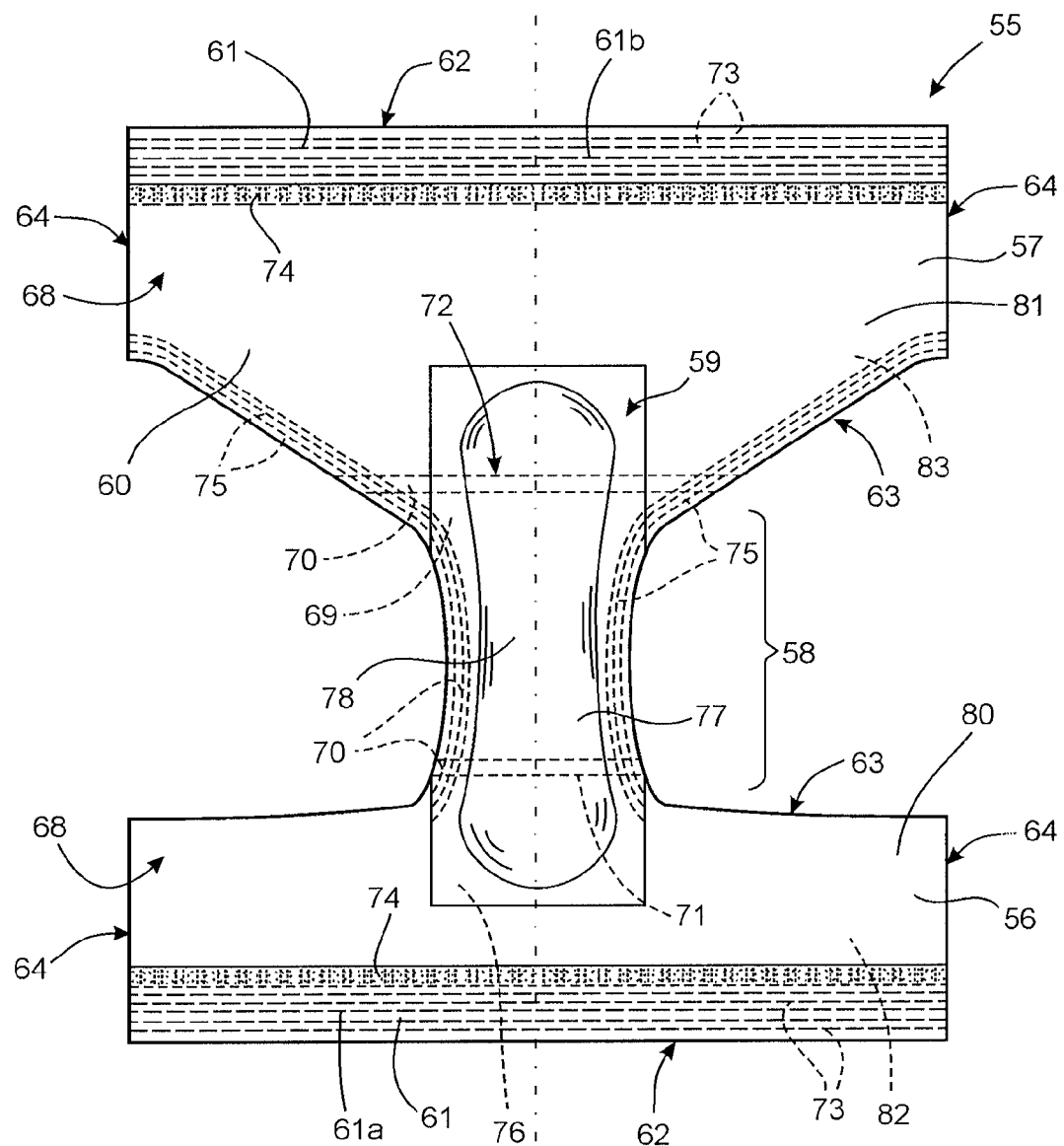
FIG. 8 shows a planar view of a pant-type diaper with the side joins open.

A second type of reinforcement layer 8 is shown in FIG. 4. The reinforcement layer 8 is a bonded nonwoven layer having more than 50% of its constituent fibres or filaments oriented in the second direction CD, and preferably more then 70% of the fibres or filaments oriented in the second direction, CD. The nonwoven layer in FIG. 8 is shown as having a multitude of bonded areas 11. However, it is alternatively conceivable to use nonwovens having other types of bond patterns such as linear bonds, or nonwovens being homogeneously bonded by bonding techniques such as through-air bonding, powder bonding or hydroentangling.

Figure 5:
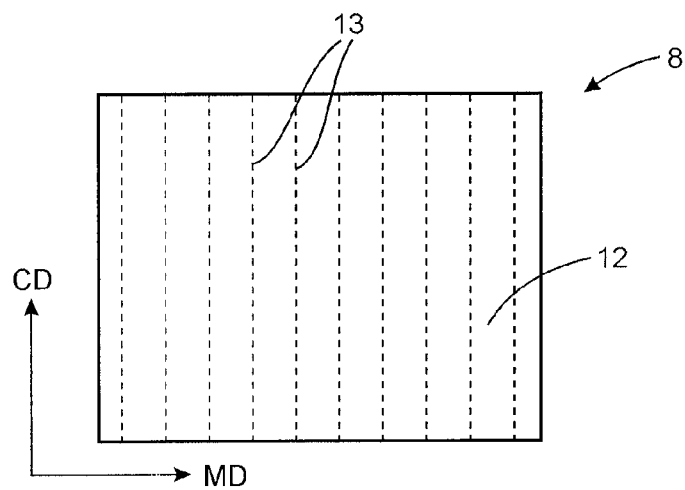
FIG. 5 shows a reinforcement layer in the form of a plastic film, before activation.
Figure 6:
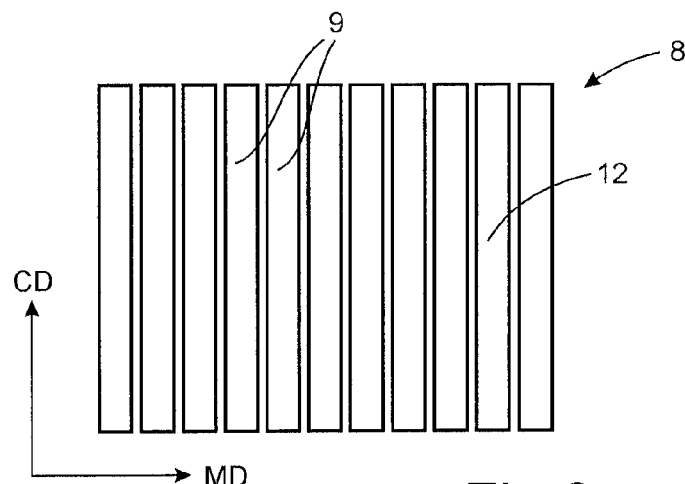
FIG. 6 shows the reinforcement layer in FIG. 5 after having been subjected to activation treatment.

FIGS. 5 and 6 show a reinforcement layer 8 in the form of a plastic film 12. The film is preferably somewhat stretchable, at least in the second direction CD. In FIG. 5, the film is shown as it appears before the elastic laminate has been subjected to activation. The film 12 is provided with a plurality of tear indications 13, arranged parallel with the second direction CD. The tear indications may be in the form of perforations, embossments, thinned portions of the film, etc.

After having been run through an activation process, the film will have the appearance shown in FIG. 6. Hence, the film 12 will be broken or torn along the tear indications 13 into band-shaped strips or filaments 9 that act as reinforcement in the laminate 1 in accordance with the invention.

Figure 7:
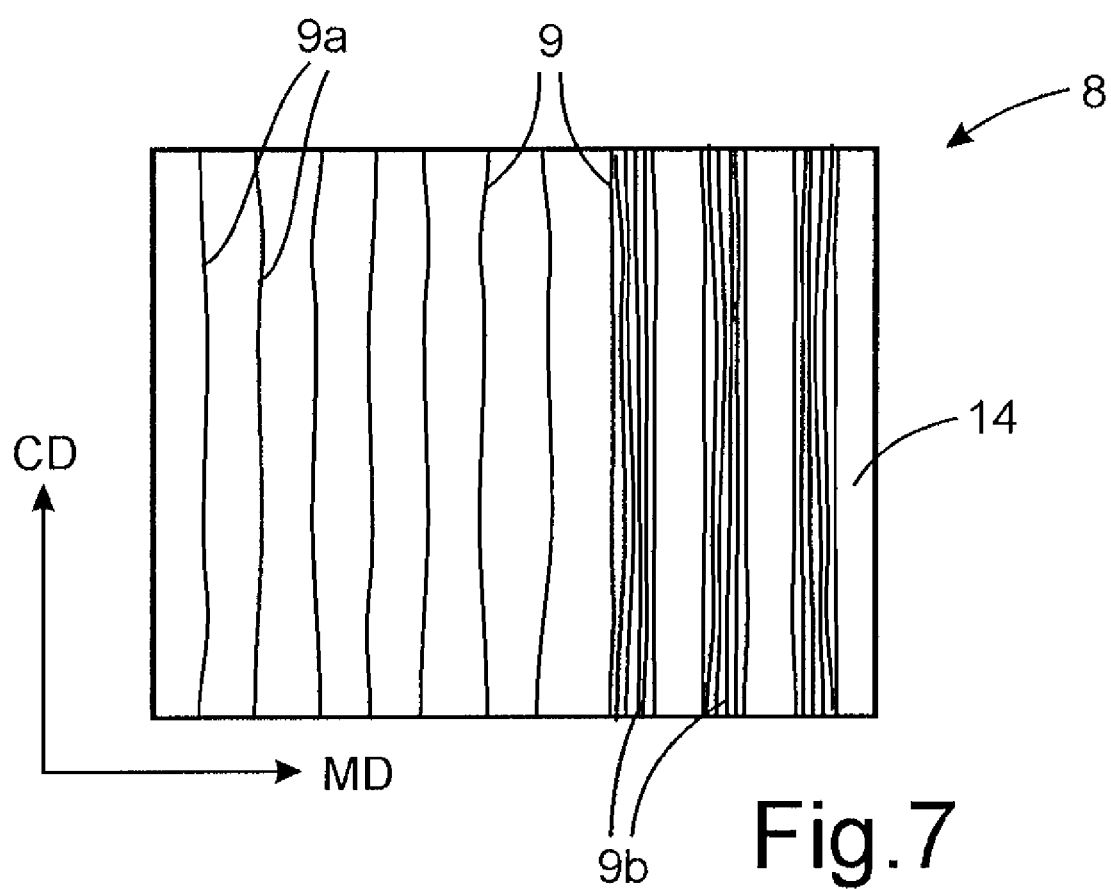
FIG. 7 shows a reinforcement layer in the form of endless fibres.

The reinforcement layer in FIG. 7 comprises a supporting layer 14 to which reinforcement fibres or filaments 9 have been attached. The supporting layer 14 serves the same purpose as the connecting strands 10 in the FIG. 3 net. Hence, the supporting layer 14 should either be made to be breakable in the activation process, should be elastic or be a thermoplastic film or fibre layer that can be broken by being subjected to heat. The thermoplastic film or fibre layer may be a hot melt adhesive. FIG. 7 shows two embodiments of reinforcement fibres or filaments 9 which can be used together but are more likely to be used separately. Accordingly, FIG. 7 shows a first set of reinforcement filaments 9*a* arranged as individual filaments and a second set of reinforcement fibres or filaments 9*b* arranged in bundles (tow).

The distance between the individual filaments 9 in the reinforcement layer 8 in accordance with the invention should preferably not exceed 30 millimetres, more preferably not exceed 20 millimetres and most preferably not exceed 15 millimetres. By arranging the reinforcement filaments 9 at a maximum distance, the puncture resistance of the laminate is improved and the risk of perforating the laminate with a finger is reduced. However, it is not critical that the distance between the filaments is precisely adapted to a finger's width, since the tensile strength and relative in-extensibility in the reinforcement filaments 9 together with the bonds in the laminate 1 counteract stretching and deformation of the material in the second direction, CD.

Figure 9:
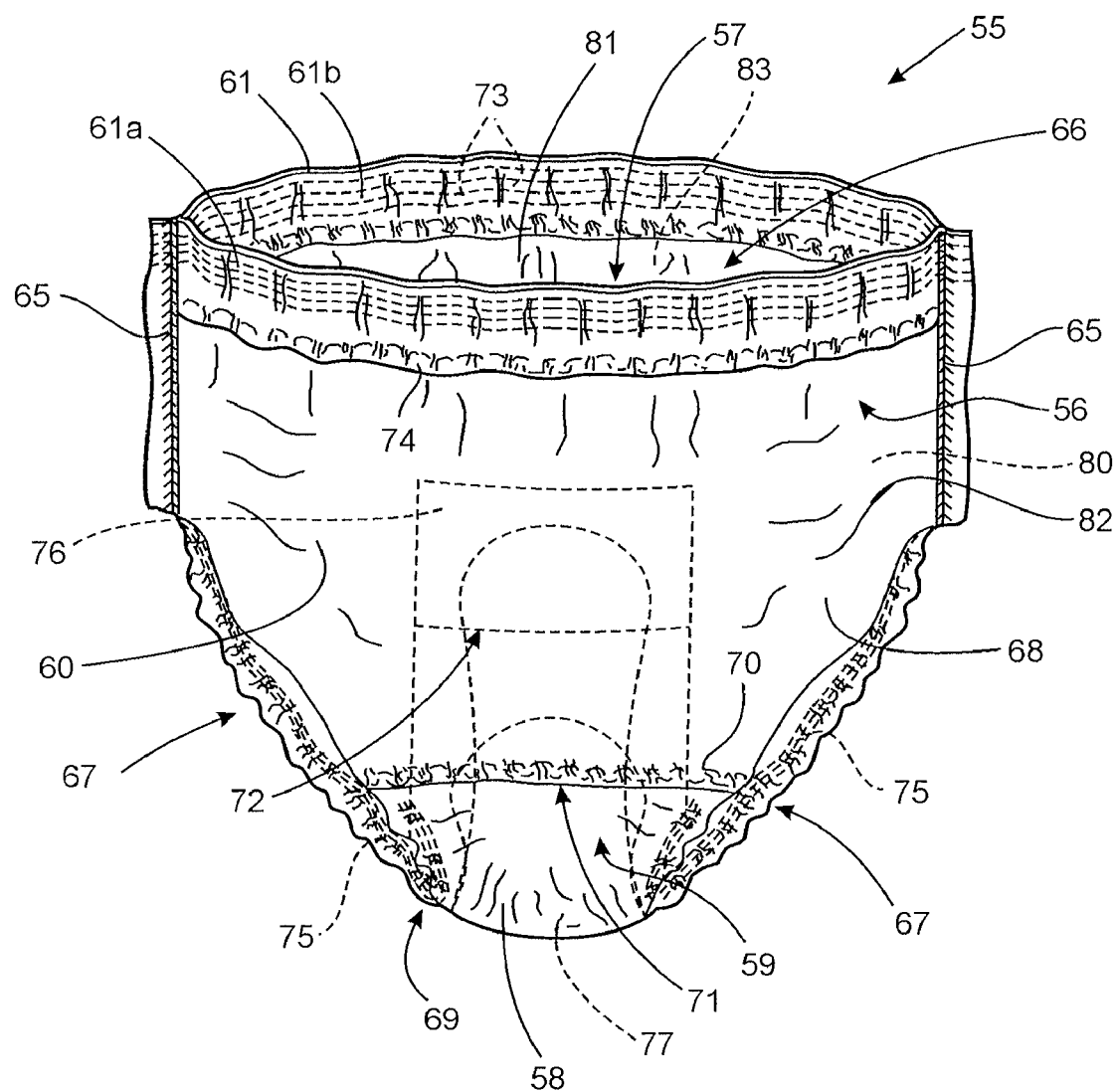
FIG. 9 shows the diaper in FIG. 8 with closed side joins.

The pant diaper 55 shown in FIGS. 8 and 9 is designed to enclose the lower part of a wearer's trunk like conventional underwear. In FIG. 8, the diaper 55 is shown from the inside, i.e. from the side facing the wearer when the article is being worn and in FIG. 9, the diaper is shown from the outside, or the garment-facing side, which is the side that is facing away from the wearer when the diaper is being worn.

The diaper has a front panel 56, a back panel 57 and a crotch panel 58 extending between the front and back panels 56,57 and having a relatively narrow width as compared to the front and back panels 56,57. The front and back panels 56,57 are arranged to cover the wearer's hips and to extend over the belly and the back of the wearer to encircle the lower part of the wearer's trunk.

The diaper 55 further comprises a core region 59 extending from the crotch panel 58 into the front panel 56 and the back panel 57. The front and back panels 56,57 form part of a chassis 60 that extends on the garment-facing side of the diaper 55 and covers and surrounds the core region 59. The chassis 60 comprises the front panel 56, the back panel 57, the crotch panel 58 and an elastic waist band 61 secured to the front and back panels 56,57. Each of the front and back panels 56,57 has a waist edge 62 a crotch edge 63 and a pair of side edges 64 respectively.

The term "panel" is used herein to denote a functional part of the diaper chassis while the terms "region" and "portion" are used to denote the location of a particular feature of the diaper in the chassis or to describe the intended positioning of a particular part of the diaper in relation to a user's body. A panel may be a separate component or an integrated part of the chassis. A region or portion may have an extension fully or partially covering one or more panels.

When components are joined, attached or secured to each other they are separate parts that have been bonded by any suitable means such as adhesively, by stitching or by ultrasonic welding or thermo-welding. The term joined also includes separable (openable) joins, such as separable side joins and reclosable joins such as hook- and loop joins, reclosable tape joins, snap fasteners, etc. Components that have been arranged on each other need not be bonded, although as used herein, the term "arranged" is broadly used to also include bonded components.

The front and back panels 56,57 are joined to each other along their side edges 64 by thermobonding, ultrasonic welding, glue strings or the like to form side seams 65, as shown in FIG. 9. The elastic waist band 61 consists of a front waist panel 61*a* and a back waist panel 61*b*, which are secured to the front panel 56 and the back panel 57, respectively. The front and back waist panels 61*a*, 61*b* are also joined to each other along the side seams 65. By joining the front and back panels 56, 57 and the waist panels 61*a*, 61*b*, the pant diaper 55 is provided with a waist opening 66 and a pair of leg openings 67.

FIG. 8 shows the diaper 55 in a flat state with any elastic components that have been attached to the chassis 60 under tensional stress drawn out to the full non-tensioned dimensions of the chassis 60. FIG. 9 shows the pant diaper 55 as it appears when the side seams 65 have been formed and the tensioned elastic elements have been allowed to relax and gather the chassis material to form elasticized leg and waist openings 67,66.

The front and back panels 56,57 are constituted by a reinforced elastic laminate 68 in accordance with the invention.

The front and back panels 56,57 are elastically stretchable in the direction of the waist edges 62.

The crotch panel 58 is formed from a nonwoven crotch material 69 that has been joined to the front and back panels 56,57 at crotch seams 70. Hence, the crotch material 69 which preferably is a non-elastic material, such as a non-elastic nonwoven material that is non-elastic at least in the transverse direction of the pant diaper, is arranged in the core region 59 of the pant diaper and overlaps slightly with the elastic front and back panels 56,57. The crotch material 69 is joined along its transverse edges 71,72 to the front and back panels 56,57 at the overlapping portions. The joining can be made in any suitable way such as by ultrasonic welding, adhesively or similar. In alternative embodiments of the invention, an outer nonwoven material may extend continuously over the front and back panels 56, 57 and the crotch panel 58 so that no seams or joins are needed between the panels 58,56,57.

In the shown example, the elastic waist band 61 comprises first and second plies of substantially non-elastic nonwoven material that is elasticized by one or more elongate elastic members 73, such as elastic threads or bands. The first and second plies can be formed from a single layer of material that is folded over onto itself or can be made from two separate strips of material. The elastic members 73 are arranged in the waist band 61 in a tensioned state such that they contract and gather the nonwoven material in the waist band 61 when they are allowed to relax, as shown in FIG. 9.

The elastic waist band 61 is secured to the front and back panels 56,57 with the elastic members 73 in an extended state and with the material in the front and back panels sandwiched between the nonwoven plies in the waist band. Alternatively, the elastic waist band 61 can be a component that is prefabricated and joined to the outside or the inside of the front and back panels 56,57 respectively. The waist band join 74 between the waist band 61 and the front and back panels 56,57 can be made in any suitable way such as by means of ultrasonic welding, heat welding, or adhesively. A further option is to create the waist band 61 from one or more non-elastic nonwoven layers that are also parts of the front and back panels 56,57 and form continuous extensions thereof. It is also conceivable to form an elastic waist feature by double-folding portions along the waist edges 62 of the elastic front and back panels 56,57 and optionally supplementing the folded portions by additional elastic elements. Suitable elastic waist bands are also disclosed in PCT/SE205/000309.

Elastic members 75 are also arranged at the edges of the leg openings 67 and serve to elasticize the leg openings. The elastic members at the leg openings can be any kind of conventional elastic elements such as elastic threads, bands, foam strips, or similar. One example of a suitable way of arranging leg elastics is disclosed in WO 2004/078083.

The planar extension of the core region 59 is defined by a liquid-impervious barrier sheet 76 arranged between an absorbent core 77 and the chassis 60. The liquid-impervious barrier sheet 76 has rectangular shape and the absorbent core 77 is hour-glass shaped. A liquid permeable topsheet 78 is arranged over the core 77 and the liquid-impervious barrier sheet 76. Hence, the liquid-impervious barrier sheet 76 underlies the absorbent core 77 and the adjacent areas immediately outside the absorbent core 77.

The liquid-permeable topsheet 78 can consist of any material known for the purpose, such as a layer of nonwoven material, a perforated plastic film, net material, tow, or the like. The topsheet 78 can, of course, also consist of a laminate of two or more sheets of the same or different material.

The liquid-impervious barrier sheet 76 can consist of a liquid-impermeable plastic film, a nonwoven sheet which has been coated with a liquid barrier material, or some other flexible material sheet which has the ability to withstand liquid penetration. However, it can be advantageous if the liquid-impervious barrier sheet 76 has a certain breathability, i.e. permits the passage of water vapour through the sheet 76.

The absorption core 77 can be made up of absorbent material, such as cellulose fluff pulp, tissue, absorbent foam, etc. It is also possible for the absorption core to contain superabsorbents, i.e. polymer materials which are able to absorb body fluid corresponding to many times their own weight and form a hydrogel. Such superabsorbents are usually present in the form of particles, but fibres, flakes, granules and films are also available. Moreover, the absorption core 77 can comprise nonabsorbent components such as stiffening elements, shaping elements, binders, etc. Various types of liquid-receiving porous structures such as fibre wads, open-cell foam or the like can also be included in the core. It is, of course, also possible to use absorption cores 77 having other shapes than that shown in FIGS. 8 and 9.

The topsheet 78, barrier sheet 76 and absorption core 77 may be formed as a separate component or "core pack" has been integrated in the diaper chassis. The various components included in the core pack can be connected to one another in any conventional manner, for example by adhesive bonding, ultrasonic welding or thermowelding. The core pack can of course contain further components in addition to those described here, such as a liquid transport sheet, elastic members, shape-stabilizing members, shaping elements or the like.

The nonwoven material 69 in the crotch panel 58 is arranged on the garment-facing side of the liquid-impervious barrier sheet 76. The core region 59 extends into the front and back panels 56,57 so that the elastic laminate 68 in these panels overlap with the liquid-impervious barrier sheet 76 in the outer parts of the core region 59 as seen in FIG. 8. The elastic laminate 68 is arranged on the garment-facing side of the liquid-impervious barrier sheet 76.

As shown in FIGS. 8 and 9, the elastic reinforced laminate 68 preferably forms the front and the back panels 56,57 of the pant diaper 55. However, it is possible to make only parts of the respective front and back panel 56,57 of the elastic reinforced laminate 68. In such embodiments, at least 20%, preferably at least 25%, more preferably at least 30% and most preferably at least 40% of the total surface area of the chassis as seen in the flat state shown in FIG. 8 is constituted by the elastic laminate in accordance with the invention. As an example, the elastic laminate may be used only in those parts of the front and back panels 56,57 that are intended to lie over the wearer's hips and thus form elastic side panels. In some instances, it may be desirable to avoid any overlap between the core region 59 and the elastic laminate material in the front and back panels 56,57.

Description of Test Methods

Tensile Strength (Reference: ASTM D 882)

The method measures tensile strength and elongation of different elastic materials. The tensile strength and elongation of a well-defined test piece is tested by means of a tensile tester.

Apparatus: Instron 456

Tensile tester connected to a computer

Crosshead speed: 500 mm/min

Clamp distance: 50 mm

Sample preparation: Test samples are cut from the entire width of the material. The width of the sample shall be 25.4 mm and the length at least 50 mm longer than the clamp distance if possible. It is of importance that the edges of the sample are even and without break notches. The samples are conditioned for at least 4 h in 50% RH±5% RH and 23° C.±2° C. before testing.

Procedure: The tensile tester is calibrated according to the apparatus instructions and set to zero. The sample is mounted and it is ensured that it is not obliquely or unevenly fastened. The material is prevented from slipping by using clamps covered with gallon or similar material. The tensile tester is started, and stopped after the material has broken (if not automatically controlled). Measurements resulting from premature failure (i.e. the sample breaks at the clamp, or is damaged during preparation) are ignored, if possible.

The following results are expressed by the tensile tester/computer:
 Maximum force, N/25.4 mm
 Elongation at maximum force, %
 Break force, N/25.4 mm
 Elongation at break force, %
 Knee point, N/%

Elasticity Test

The method measures how an elastic material behaves at cycles of repeated load and unload. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:
 Crosshead speed: 500 mm/min
 Clamp distance: 50 mm
 Preload: 0.05 N The sample is placed in the clamps according to the marks and it is made sure that the sample I centred and fastened perpendicularly in the clamps. The tensile tester is started and three cycles between 0 and the predetermined elongation equal to the highest defined $1^{st}$ load are performed. Before the last cycle, the sample is relaxed for 1 minute, then the permanent elongation is measured by stretching the sample until a force of 0.1 N is detected and the elongation is read.

An elastic material is defined as a material having a permanent elongation after relaxation of less than 10% after the material has been subjected to an elongation of 30% in the test above. An elongation of 30% means an elongation to a length that is 30% longer than the initial length of the sample.

A non-elastic material has a permanent elongation after relaxation of more than 10% after having been subjected to an elongation of 30%.

Puncture Strength

Puncture strength is measured according to ASTM Designation D3763-02. From penetration impact-type tests, this method produces data of load versus displacement. The maximum load for each sample is calculated.

The invention claimed is:

1. An elastically stretchable laminate comprising a first non-elastic nonwoven web, a second non-elastic nonwoven web and an elastic film between the first and the second nonwoven webs wherein the laminate has been rendered elastic in a first direction by incremental stretching and partial tearing of the first and second nonwoven webs, wherein the laminate further comprises a reinforcement layer arranged between the first and second non-elastic nonwoven webs and comprising unbroken reinforcement fibres or filaments extending in a second direction, generally perpendicular to the first direction.

2. An elastically stretchable laminate in accordance with claim 1, wherein the reinforcement layer is an oriented fibrous nonwoven layer having more than 50% of the fibres oriented in the second direction.

3. An elastically stretchable laminate in accordance with claim 2, wherein the nonwoven reinforcement layer is a spunbond or carded nonwoven layer.

4. An elastically stretchable laminate in accordance with claim 1, wherein the reinforcement layer comprises a bonded or unbonded layer of endless filaments.

5. An elastically stretchable laminate in accordance with claim 4, wherein the endless filaments are bonded to a supporting layer.

6. An elastically stretchable laminate in accordance with claim 4, wherein the distance between the individual filaments does not exceed 30 millimetres.

7. An elastically stretchable laminate according to claim 6, wherein the distance between the individual filaments does not exceed 15 millimeters.

8. An elastically stretchable laminate in accordance with claim 1, wherein the reinforcement layer is a net.

9. An elastically stretchable laminate in accordance with claim 8, wherein the net has a first set of filaments running in the first direction and a second set of filaments running in the second direction and constituting reinforcement filaments, the first set of filaments having lower tensile strength than the second set of filaments.

10. An elastically stretchable laminate in accordance with claim 1, wherein the reinforcement layer is a plastic film.

11. An elastically stretchable laminate in accordance with claim 1, wherein the reinforcement layer has been provided with tear indications arranged in the second direction and along which the reinforcement layer has been fully or partially broken during activation of the laminate.

12. An elastically stretchable laminate in accordance with claim 10, wherein the reinforcement layer is in the form of elongated strips of material extending in the second direction.

13. An elastically stretchable laminate in accordance with claim 1, wherein at least one of the non-elastic nonwoven webs is a creped nonwoven.

14. An elastically stretchable laminate in accordance with claim 1 wherein the elastic film is a perforated film.

15. A pant absorbent article comprising a chassis structure comprising a front panel having a front end edge and first and second side edges, a back panel having a back end edge and first and second side edges,
 a crotch panel arranged between the front and back panels
  front and back waist panels arranged at the front and back panels, respectively, and a core being integrated with the chassis structure, the first and second side edges of the front panel being joined by edge joins to the corresponding first and second side edges of the back panel, at least one of the front and back panels comprising an elastic laminate comprising a first non-elastic nonwoven web, a second non-elastic nonwoven web and an elastic film between the first and the second nonwoven webs wherein the laminate has been rendered elastic in a first direction by incremental stretching and partial tearing of the first and second nonwoven webs, wherein the laminate further comprises a reinforcement layer arranged between the first and second non-elastic nonwoven webs and comprising unbroken reinforcement fibres or filaments extending in a second direction, generally perpendicular to the first direction.

16. A pant absorbent article according to claim 15, wherein the elastic laminate forms the front and back panels of the pant absorbent article.

17. A pant absorbent article according to claim 15, wherein the elastic laminate constitutes at least 20% of the total surface area of the chassis.

18. A pant absorbent article according to claim 17, wherein the elastic laminate constitutes at least 40% of the total surface area of the chassis.

19. A pant absorbent article according to claim 15, wherein the reinforcement layer is an oriented fibrous nonwoven layer having more than 50% of the fibres oriented in the second direction.

20. A pant absorbent article according to claim 19, wherein the nonwoven reinforcement layer is a spunbond or carded nonwoven layer.

21. A pant absorbent article according to claim 15, wherein the reinforcement layer is a layer of endless filaments.

22. A pant absorbent article according to claim 21, wherein the distance between the individual filaments does not exceed 30 millimetres.

23. A pant absorbent article according to claim 22, wherein the distance between the individual filaments does not exceed 15 millimetres.

24. A pant absorbent article according to claim 15, wherein the reinforcement layer is a net.

25. A pant absorbent article according to claim 15, wherein the net has a first set of filaments running in the first direction and a second set of filaments running in the second direction and constituting reinforcement filaments, the first set of filaments having lower tensile strength than the second set of filaments.

26. A pant absorbent article according to claim 15, wherein the reinforcement layer is a plastic film.

27. A pant absorbent article according to claim 15, wherein the reinforcement layer has been provided with tear indications arranged in the second direction and along which the reinforcement layer has been fully or partially broken during activation of the laminate.

28. A pant absorbent article according to claim 27, wherein the reinforcement layer is in the form of elongated strips of material extending in the second direction.

29. A pant absorbent article according to claim 15, wherein at least one of the waist panels comprises an elastic waist.

30. A pant absorbent article according to claim 15, wherein at least one of the non-elastic nonwoven laminate layers is a creped nonwoven web.

* * * * *